(12) United States Patent
Sakurai et al.

(10) Patent No.: US 7,967,796 B2
(45) Date of Patent: Jun. 28, 2011

(54) ADHESIVE FOR INJECTION NEEDLE, A METHOD FOR BONDING INJECTION NEEDLE, A SYRINGE FRONT-ASSEMBLY AND A SYRINGE

(75) Inventors: Yuusuke Sakurai, Osaka (JP); Jotaro Kishimoto, Hyogo (JP); Hiroshi Yoshikawa, Osaka (JP); Masahiko Kato, Osaka (JP)

(73) Assignee: Takeda Pharmaceutical Company, Osaka (JP)

( * ) Notice: Subject to any disclaimer, the term of this patent is extended or adjusted under 35 U.S.C. 154(b) by 626 days.

(21) Appl. No.: 11/921,574

(22) PCT Filed: Jun. 5, 2006

(86) PCT No.: PCT/JP2006/311213
§ 371 (c)(1),
(2), (4) Date: Dec. 5, 2007

(87) PCT Pub. No.: WO2006/132176
PCT Pub. Date: Dec. 14, 2006

(65) Prior Publication Data
US 2009/0209919 A1      Aug. 20, 2009

(30) Foreign Application Priority Data
Jun. 6, 2005   (JP) .............................. P 2005-165083

(51) Int. Cl.
*A61M 5/32* (2006.01)
*A61M 5/31* (2006.01)
*C09J 163/00* (2006.01)
*C08L 63/00* (2006.01)

(52) U.S. Cl. ........ 604/240; 604/187; 604/192; 604/199; 604/218; 525/524; 525/533; 523/457; 523/458; 156/330; 156/330.9

(58) Field of Classification Search .................. 523/400, 523/457, 458; 525/523, 524, 533; 604/19, 604/27, 187, 192, 199, 218, 240; 156/330, 330.9, 331.1
See application file for complete search history.

(56) References Cited

U.S. PATENT DOCUMENTS
3,390,678 A * 7/1968 Bradley et al. ................ 604/240
(Continued)

FOREIGN PATENT DOCUMENTS
JP           57-14437           1/1982
(Continued)

OTHER PUBLICATIONS
Abstract of JP 59-204675 A, provided by the JPO website (no date).*
(Continued)

*Primary Examiner* — Michael J Feely
(74) *Attorney, Agent, or Firm* — Wenderoth, Lind & Ponack, L.L.P.

(57) ABSTRACT

The present invention inhibits the occurrence of the foreign matters attributable to an adhesive for bonding an injection needle to a needle-base member so as to enhance the yield of a syringe when producing the same. A front-assembly (3) additionally provided at a leading end of an injection cylinder (2) comprises an injection needle (4), a needle-base member (5), a connection hub (6) and a protector cap (7). The injection needle (4) and the needle-base member (5) are fixed to each other with an epoxy adhesive (19). This adhesive (19) contains denatured aliphatic epoxy resin in the amount set to about 10 to about 25 wt % and its viscosity is set to about 20000 to about 40000 mPa·s. This adhesive (19) is heated at a temperature of at least 130 degrees C. for about 20 minutes to cure it. After the front-assembly (3) and the injection cylinder (2) have been sterilized with vapor, the connection hub (6) has a connection portion (17) external fitted and secured to the leading end of the injection cylinder (2).

5 Claims, 4 Drawing Sheets

U.S. PATENT DOCUMENTS 4,308,311 A * 12/1981 Ogawa et al. ............... 428/215
4,795,445 A    1/1989 Jensen
5,358,491 A * 10/1994 Johnson et al. ............. 604/232

FOREIGN PATENT DOCUMENTS

| | | | |
|---|---|---|---|
| JP | 59-204675 A | * | 11/1984 |
| JP | 64-64670 | | 3/1989 |
| JP | 10-25391 | | 1/1998 |
| JP | 11-302358 | | 11/1999 |
| JP | 2002-146321 | | 5/2002 |
| JP | 2004-323589 | | 11/2004 |

OTHER PUBLICATIONS

Research Disclosure 42620: "Epoxy polyamide compositions for flexible circuits", disclosed anonymously (Oct. 1999).*

Translation of JP 59-204675 A, provided by the USPTO translations branch (no date).*

International Search Report issued Oct. 3, 2006 in the International (PCT) Application of which the present application is the U.S. National Stage.

* cited by examiner

Fig. 4

COMPARISON TABLE 1  RELATIONSHIP BETWEEN VISCOSITY OF ADHESIVE AND RATE OF OCCURRENCE OF FOREIGN MATTERS

|  | VISCOSITY OF ADHESIVE (mPa·s) | FILLING ABILITY OF ADHESIVE | CONTENT OF DENATURED ALIPHATIC EPOXY RESIN (%) | CURING TEMPERATURE (°C) | OCCURRENCE RATE OF FOREIGN MATTERS (%) |
|---|---|---|---|---|---|
| EXAMPLE 1 | 20000 | ○ | 15~25 | 120 | 0.1~1.2 |
| EXAMPLE 2 | 30000 | ○ | 10~20 | 120 | 0.0~0.5 |
| COMPARISON EXAMPLE 1 | 10000 | ◎ | 15~25 | 120 | about 1~15 |

Fig. 5

COMPARISON TABLE 2  RELATIONSHIP BETWEEN CURING TEMPERATURE OF ADHESIVE AND OCCURRENCE RATE OF FOREIGN MATTERS

|  | CURING TEMPERATURE (°C) | VISCOSITY OF ADHESIVE (mPa·s) | FILLING ABILITY OF ADHESIVE | CONTENT OF DENATURED ALIPHATIC EPOXY RESIN (%) | OCCURRENCE RATE OF FOREIGN MATTERS (%) |
|---|---|---|---|---|---|
| EXAMPLE 3 | 130 | 10000 | ◎ | 15~25 | 0.0~0.3 |
| EXAMPLE 4 | 130 | 20000 | ○ | 15~25 | 0.0 |
| EXAMPLE 5 | 130 | 30000 | ○ | 10~20 | 0.0 |
| COMPARISON EXAMPLE 1 | 120 | 10000 | ◎ | 15~25 | about 1~15 |

ADHESIVE FOR INJECTION NEEDLE, A METHOD FOR BONDING INJECTION NEEDLE, A SYRINGE FRONT-ASSEMBLY AND A SYRINGE

This application is a U.S. national stage of International Application No. PCT/JP2006/311213 filed Jun. 5, 2006.

TECHNICAL FIELD

The present invention relates to an adhesive agent used for bonding an injection needle and a method for bonding the injection needle and more particularly it concerns an adhesive agent for an injection needle and a method for bonding the injection needle, which inhibits the occurrence of foreign matters attributable to the adhesive agent so as to enhance the yield, as well as a syringe front-assembly using the same and a syringe.

BACKGROUND ART

A general example of the syringes comprises a front-assembly, which is provided with an injection needle, a needle-base member, a protector cap and a connection hub, secured to a leading end of an injection cylinder (for example, see Patent Literature 1).

The connection hub has a connection portion hermetically and securely fixed to the leading end of the injection cylinder and has the needle-base member detachably attached thereto. The injection needle has a base end portion secured to the needle-base member and a protector cap is removably fitted onto the injection needle so as to cover a periphery thereof.

The base end portion of the injection needle is assuredly secured to the needle-base member and is bonded thereto with an epoxy adhesive consisting mainly of bisphenol A-type epoxy resin. More specifically, the needle-base member has the leading end portion provided with a hole for inserting the base end portion of the injection needle. The adhesive is hermetically filled into a space between the base end portion of the injection needle and the needle-base base member so as not to cause a bad appearance such as roping. Conventionally, such an adhesive has a viscosity set to about 10000 mPa·s by adjusting the content of denatured aliphatic epoxy resin.

Although the epoxy resin adhesive agent is cured by heating, there are many cases where the needle-base member is formed from polypropylene resin and the like synthetic resin material. Adopted for the adhesive are those of the type that cures quickly at a relatively low temperature of about 100 degrees C., for example, below 120 degrees C., so that the needle-base member does not suffer from thermal deformation upon curing.

And the injection needle and the front-assembly with this injection needle are assembled to an injection cylinder during the production process of the syringe and thereafter are subjected to a sterilization treatment with dump and heat by vapor at a temperature of, for example, 121 degrees C. in an aseptic room before they are filled with injection medicine or are assembled to an injection cylinder prefilled with the injection medicine.

Patent Literature 1: Utility Model Application Laid-Open No. 10-211280

DISCLOSURE OF THE INVENTION

The Problem the Invention Intends to Solve

The denatured aliphatic epoxy resin has a poor reactivity on curing. Even if the reaction time is extended at the above curing temperature, much non-reacted one, which occupies, for example about 20% of the whole amount, remains. Since this non-reacted denatured aliphatic epoxy resin is generally dissolved in water having a temperature of at least 70 degrees C., there is a case where it is dissolved out of the adhesive cured on conducing the vapor sterilization treatment and is condensed to become a foreign matter after the sterilization treatment, which adheres to a tip of the injection needle or an inner surface of the protector cap. The syringe with this non-reacted denatured aliphatic epoxy resin adhered thereto as a foreign matter is excluded as a product of bad appearance through an inspection treatment with the result of being not easy to improve the yield. This has become a problem when implementing the vapor sterilization treatment industrially.

The present invention has a technical object to solve the above-mentioned problem and provide an adhesive for an injection needle and a method for bonding the injection needle, which are able to inhibit the occurrence of foreign matters attributable to the adhesive for enhancing the yield, as well as a syringe front-assembly and a syringe.

Means for Solving the Problem

The present invention is constructed as follows so as to accomplish the above-mentioned object, for example, if it is explained based on FIGS. 1 to 5 which show embodiments of the present invention.

More specifically, a first invention concerns an adhesive for an injection needle. The adhesive consists of an epoxy adhesive containing denatured aliphatic epoxy resin and bonds a base end portion of an injection needle 4 to a needle-base member 5 at a leading end of an injection cylinder 2, a viscosity of which is at least about 20000 mPa·s.

Here, like the viscosity of "about 20000", the word "about" attached to a numerical value in the recitation of the specification and claims includes an allowable difference of ±5%.

According to the first invention, the viscosity is as high as about 20000 mPa·s. Consequently, it suffices if the denatured aliphatic epoxy resin is contained in a small quantity with the result of alleviating the non-reacted denatured aliphatic epoxy resin residual in the adhesive after it has cured.

It is sufficient if the adhesive has the viscosity of at least about 20000 mPa·s. But when it is excessively high, there is a likelihood that the excessively high viscosity reduces the workability on filling the adhesive. For this reason, it is preferably set to not more than about 40000 mPa·s, more preferably not more than about 30000 mPa·s. This enables the adhesive to be easily filled into a space between the injection needle and the needle-base member without causing the bad appearance because of roping.

The content of the denatured aliphatic epoxy resin is concretely set to about 10 to about 25 wt % and more preferably set to about 20 wt % of the total quantity of the epoxy adhesive.

Further, the adhesive may additionally contain bisphenol A-type epoxy resin, denatured polyamide resin and titanium oxide.

A second invention relates to a method for bonding an injection needle, more specifically a method for bonding an injection needle 4 to a needle-base member 5 at a leading end of an injection cylinder 2 with an epoxy adhesive 19. The adhesive 19 is filled into a space between the injection needle 4 and the needle-base member 5 and then is heated at a temperature of at least about 130 degrees C. to cure it.

According to the second invention, the curing temperature is set to be as high as at least about 130 degrees C. Therefore, even if the denatured aliphatic epoxy resin of poor reactivity is contained, the polymerization reaction is accelerated to result in alleviating non-reacted denatured aliphatic epoxy resin residual in the adhesive after curing.

In this case, the adhesive may have a viscosity as low as, for example, about 10000 mPa·s and therefore can be readily filled into the space between the injection needle and the needle-base member without causing the bad appearance such as roping.

It is required to maintain the heating temperature for curing the adhesive, namely the curing temperature at a temperature lower than a softening temperature of the needle-base member. In consequence, if this needle-base member comprises polypropylene resin or the other synthetic resin material which softens, for example, at about 160 degrees C., the curing temperature is preferably set to not more than about 140 degrees C. and more preferably to about 130 degrees C.

However, this curing temperature is satisfactory as far as it does not exert bad influence on the injection needle, the needle-base member or the adhesive. For instance, when the needle-base member is formed from a material of excellent heat resistance such as stainless steel, the curing temperature can be set to a higher one, for example, about 150 degrees C. so as to reduce the quantity of the residual non-reacted denatured aliphatic epoxy resin.

The heating time for curing purpose is sufficient as long as the epoxy resin is fully cured. Concretely, it is set to about 5 to about 30 mins. and more preferably to about 10 to about 20 mins. Short heating time may cause a fear of not only increasing the residual amount of non-reacted substance but also insufficiently curing the epoxy resin. This is because on one hand, once the epoxy resin has sufficiently cured, even if the heating time is excessively extended, it is difficult to more reduce the residual amount of the non-reacted substance and further the efficiency of the curing treatment is decreased.

The epoxy adhesive concretely may include bisphenol A-type epoxy resin, denatured aliphatic epoxy resin, denatured polyamide resin and titanium oxide. In this case, although the content of the denatured aliphatic epoxy resin is not limited to specific numerical value, it is usually set to about 10 to about 25 wt % and more preferably to not more than about 20 wt %.

Besides, a third invention concerns a syringe front-assembly. This syringe front-assembly comprises the injection needle 4, the needle-base member 5, a connection hub 6 and a protector cap 7. The injection needle 4 is fixed to the needle-base member 5, which is detachably attached to the connection hub 6. This connection hub 6 is provided with a connection portion 17 which is secured to a leading end of the injection cylinder 2. The protector cap 7 is removably fitted onto the injection needle 4 in such a manner that it covers a periphery of the injection needle 4. The injection needle 4 is fixed to the needle-base member 5 mutually with the adhesive 19 for injection needle according to the first invention.

Additionally, a fourth invention concerns another syringe front-assembly. This syringe front-assembly comprises the injection needle 4, the needle-base member 5, the connection hub 6 and the protector cap 7. The injection needle 4 is fixed to the needle-base member 5, which is detachably attached to the connection hub 6. This connection hub 6 is provided with the connection portion 17 which is secured to the leading end of the injection cylinder 2. The protector cap 7 is removably fitted onto the injection needle 4 in such a manner that it covers the periphery of the injection needle 4. The injection needle 4 is fixed to the needle-base member 5 mutually by the method for bonding the injection needle according to the second invention.

A fifth invention relates to a syringe. This injection cylinder 2 has a leading end which is additionally provided with a needle-base member 5. The injection needle 4 is fixed to the needle-base member 5 and the protector cap 7 is removably fitted onto the injection needle 4 so that it covers the periphery of the injection needle 4. The injection needle 4 is mutually secured to the needle-base member 5 with the adhesive 19 for injection needle according to the first invention.

A sixth invention concerns a syringe which comprises an injection cylinder 2. This injection cylinder 2 has a leading end which is additionally provided with the needle-base member 5. The injection needle 4 is fixed to the needle-base member 5 and the protector cap 7 is removably fitted onto the injection needle 4 so that it covers the periphery of the injection needle 4. The injection needle 4 is mutually secured to the needle-base member 5 by the method for bonding the injection needle according to the second invention.

The above-mentioned syringe is not limited to those of a specific shape or structure but may be, for example, a uni-chamber prefilled syringe, a dual-chamber prefilled syringe or an unfilled syringe.

Effect of the Invention

Since the present invention is constituted and functions as mentioned above, it offers the following effects.

According to the first invention, the adhesive has the viscosity set to at least about 20000 mPa·s. Therefore, it contains only a small quantity of denatured aliphatic epoxy resin to result in the possibility of alleviating the non-reacted denatured aliphatic epoxy resin residual after it has been cured.

Further, according to the second invention, since the curing temperature is set to a temperature as high as at least about 130 degrees C., even if the adhesive contains the denatured aliphatic epoxy resin, it is possible to sufficiently accelerate the reaction and reduce the non-reacted denatured aliphatic epoxy resin remaining after it has been cured.

BRIEF DESCRIPTION OF THE DRAWINGS

FIG. 4 is Comparison Table 1 showing the viscosity of the adhesive and the occurrence rate of the foreign matters; and FIG. 5 is Comparison Table 2 showing a relationship between the curing temperature of the adhesive and the occurrence rate of the foreign matters.

EXPLANATION OF NUMERALS

Figure 1:
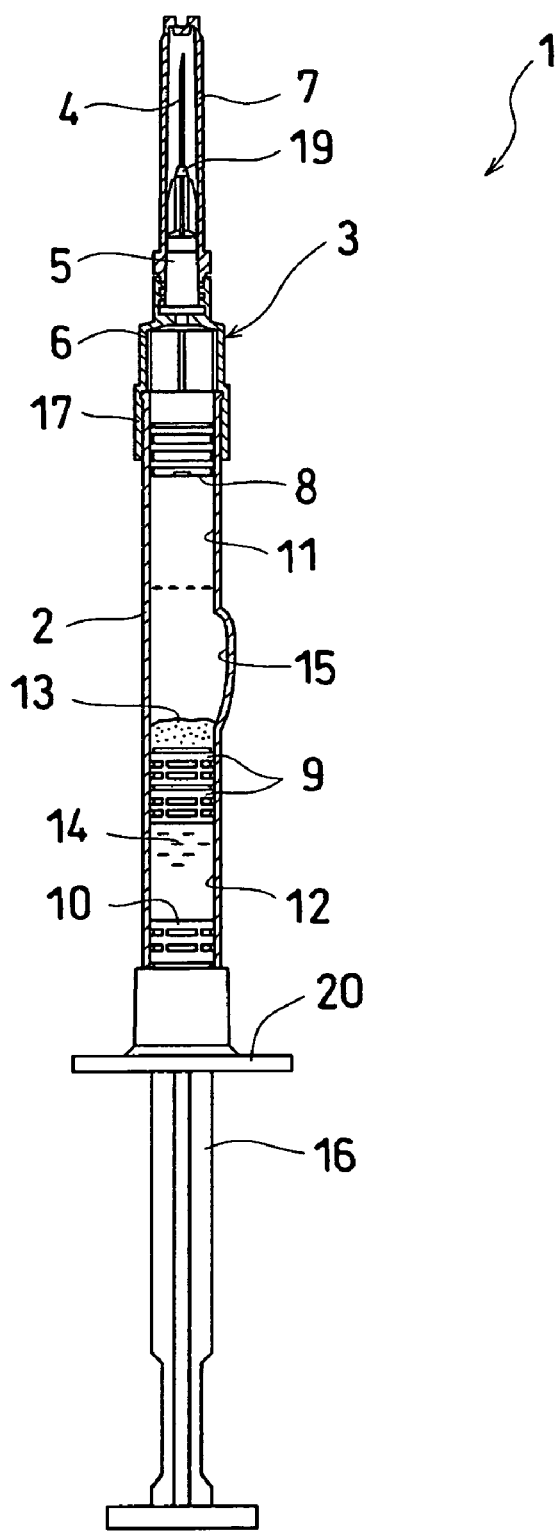
FIG. 1 is a sectional view of a dual-chamber prefilled syringe showing a first embodiment of the present invention.

1 . . . syringe (dual-chamber prefilled syringe or uni-chamber prefilled syringe)
2 . . . injection cylinder
3 . . . syringe front-assembly
4 . . . injection needle
5 . . . needle-base member
6 . . . connection hub
7 . . . protector cap
17 . . . connection portion
19 . . . adhesive for injection needle (epoxy adhesive)

MOST PREFERRED EMBODIMENT OF THE INVENTION

Hereafter, an explanation is given for the embodiments of the present invention based on the drawings.

Figure 2:
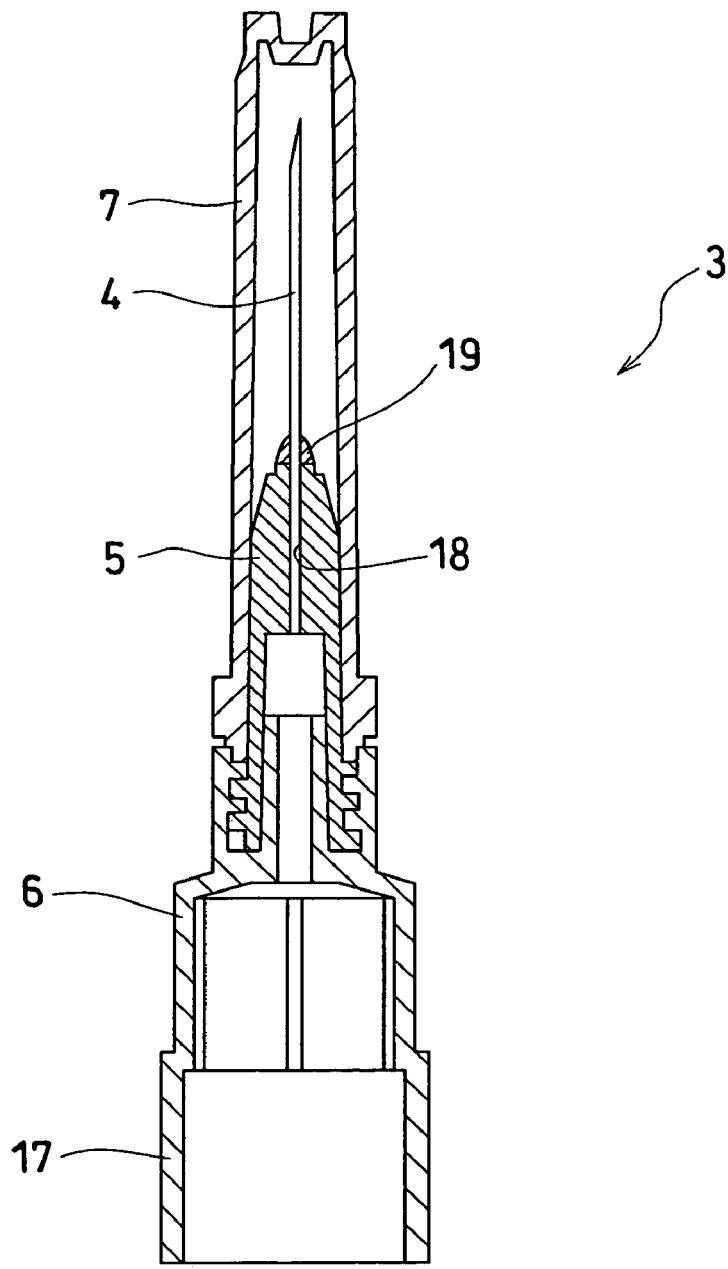
FIG. 2 is an enlarged sectional view of a front-assembly for the syringe of the first embodiment.
Figure 2:
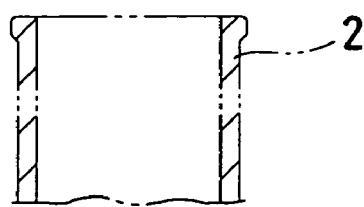

FIGS. 1 and 2 show a first embodiment of the present invention. FIG. 1 is a sectional view of a dual-chamber prefilled syringe and FIG. 2 is an enlarged sectional view of a syringe front-assembly.

As shown in FIG. 1, this syringe 1 comprises an injection cylinder 2 having a leading end to which a syringe front-assembly 3 is secured. This syringe front-assembly 3 is provided with an injection needle 4, a needle-base member 5, a connection hub 6 and a protector cap 7.

The injection cylinder 2 has an interior area partitioned into a front first chamber 11 and a rear second chamber 12 by a front plug 8, a middle plug 9 and an end plug 10. The first chamber 11 accommodates powder pharmaceutical component 13 and the second chamber 12 contains dissolving liquid or dispersing liquid 14. Further, a bypass 15 projects from a side wall of the injection cylinder 2. If the end plug 10 is advanced by a plunger 16, the middle plug 9 also advances. And when the middle plug 9 has reached a position where the bypass 15 is formed, the first chamber 11 and the second chamber communicate with each other through the bypass 15, thereby enabling the dissolving liquid 14 to flow into the first chamber so as to dissolve or disperse the pharmaceutical component 13.

The connection hub 6 is provided with a connection portion 17, which is externally fitted onto the leading end of the injection cylinder 2 for hermetical and assured securing purpose.

As shown in FIGS. 1 and 2, the connection hub 6 has a leading end to which the needle-base member 5 is detachably attached by screws. The needle-base member 5 has a leading end perforated to provide an insertion hole 18. The injection needle 4 has its base end portion inserted through this hole 18 so as to assuredly fix it to the needle-base member 5 with an epoxy adhesive 19. Besides, the protector cap 7 is detachably attached to the needle-base member 5 in such a manner that it covers a periphery of the injection needle 4.

The epoxy adhesive 19 consists of compounds that cure quickly at a low temperature. Concretely it contains bisphenol A-type epoxy resin as a main component and in addition denatured aliphatic epoxy resin, denatured polyamide resin and titanium oxide. The viscosity of this adhesive is adjusted within a range of about 10000 to about 40000 mPa·s by the content of the denatured aliphatic epoxy resin. However, it is preferable to increase the viscosity by reducing the content of the denatured aliphatic epoxy resin. These epoxy adhesives 19 are cured by heating up to at least about 120 degrees C., preferably at least about 130 degrees C.

Next, an explanation is given for the procedures of sterilization treatment carried out during the assembly process of the syringe 1.

The injection needle 4 is preliminarily bonded to the needle-base member 5 with an epoxy adhesive 19. This needle-base member 5 is secured to the leading end of the connection hub 6 by screws and the protector cap 7 is fitted around the injection needle 4 so as to assembly the syringe front-assembly 3 as shown in FIG. 2.

Subsequently, this front-assembly 3 and the injection cylinder 2, which has preliminarily accommodated the pharmaceutical component 13 and the dissolving or dispersing liquid in the respective chambers 11 and 12, are subjected to a sterilization treatment with dump and heat by vapor at a predetermined temperature within an aseptic room. Then after this sterilization treatment has finished and thy are dried, the connection hub 6 has the connection portion 17 externally fitted and fixed onto the leading end of the injection cylinder 2 and a finger grip 20 is externally fitted and fixed onto a rear end of the injection cylinder 2 so as to complete the assembly of the syringe 1. In FIG. 1, although the plunger 16 is fixed by screws to a rearward portion of the end plug 10, this plunger 16 may be removed and packed in a set as it is removed, for a product.

An inspection is performed for the appearance of the syringe 1 to see if any foreign matter is adhered to the leading end of the injection needle 4 and an inner surface of the protector cap 7 after the sterilization treatment or the assembly process has completed.

Figure 3:
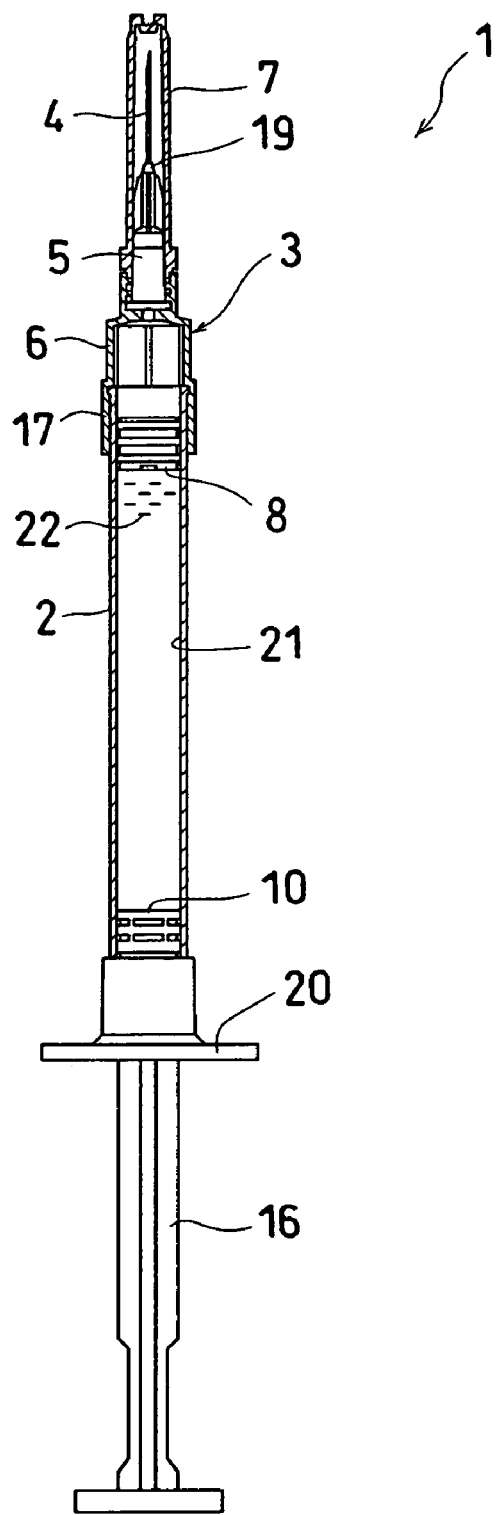
FIG. 3 is a sectional view of a uni-chamber prefilled syringe showing a second embodiment of the present invention.

FIG. 3 shows a second embodiment of the present invention and is a sectional view of a uni-chamber prefilled syringe.

As for this syringe 1, its injection cylinder 2 has an interior area partitioned hermetically from an exterior area by the front plug 8 and the end plug 10 as a chamber accommodating pharmaceutical liquid 21, which accommodates pharmaceutical medicine 22 for injection.

Regarding the syringe 1 of the second embodiment, the injection cylinder 2 has a front end additionally provided with a front-assembly 3. This front-assembly 3 is provided with the injection needle 4, the needle-base member 5, the connection hub 6 and the protector cap 7. The injection needle 4 is securely fixed to the needle-base member 5 with the epoxy adhesive 19. And other constructions are the same as those in the first embodiment. Therefore, the explanation therefor is omitted.

The syringe 1 is subjected to the sterilization treatment in the assembly process through the following procedures.

First, the front-assembly 3 has been prepared like the first embodiment. The thus prepared front-assembly 3 has the connection hub 6 externally fitted and fixed onto the leading end of the unfilled injection cylinder 2 and a finger grip 20 is externally fitted and fixed onto a rear end of the injection cylinder 2.

Next, in this state, the front-assembly 3 is subjected to the sterilization treatment with dump and heat by vapor of a predetermined temperature and the thus sterilized front-assembly 3 is dried. Then the pharmaceutical medicine for injection 22 is accommodated into the pharmaceutical liquid accommodating chamber 21 of the injection cylinder 2, which is hermetically sealed by the end plug 10 to complete the assembly process. After the completion of the sterilization treatment or the assembly process, the inspection is carried out for the appearance of the front-assembly 3 to see if any foreign matter is adhered thereto, in the same as the first embodiment.

It is to be noted that in this second embodiment, the front-assembly 3 is additionally provided at the leading end of the unfilled injection cylinder 2 and is subjected to the sterilization treatment. Then the pharmaceutical medicine 22 for injection is filled into the injection cylinder 2. However, according to the present invention, in the case of the uni-chamber prefilled syringe, needless to say, the front-assembly and the filled injection cylinder may be subjected to the sterilization treatment and then assembled to each other, like the first embodiment.

EXAMPLE

Next, the injection needle and the needle-base member were mutually bonded by differentiating the bonding conditions and then were subjected to the sterilization treatment. Subsequently, measurements were made by eyes and enlarged observation for the occurrence of foreign matters attributable to the adhesive in each case.

The combination ratio of the used adhesive is 35 to 50 wt % of bisphenol A-type epoxy resin, 10 to 25 wt % of denatured aliphatic epoxy resin and 10 to 20 wt % of titanium oxide.

As for the evaluation about the filling characteristics, it has been judged by eyes as to whether or not there occurs any bad appearance such as roping. Those without any bad appearance are marked by circle (○) and those excellent in bonding workability are marked by double circle (◎).

The sterilization treatment was conducted by applying thermal load of at least 20 mins. at a temperature of 121 degrees C. After having sterilized, the sterilized object was dried by repeating vacuum and abdominal pressure while warming the interior area of the aseptic room.

(1) Relationship Between the Viscosity of the Adhesive and the Occurrence Rate of Foreign Matters Example 1

The viscosity of the adhesive was adjusted to 20000 mPa·s with the content of the denatured aliphatic epoxy resin falling within a range of 15 to 25 wt %. The adhesive was cured by heating at 120 degrees C. for 20 mins.

As a result of having measured the sterilized adhesive, the occurrence rate of foreign matters was 0.1 to 1.2%.

Example 2

The viscosity of the adhesive was adjusted to 30000 mPa·s with the content of the denatured aliphatic epoxy resin falling within a range of 10 to 20 wt %. The adhesive was cured by heating at 120 degrees C. for 20 mins.

As a result of having measured the sterilized adhesive, the occurrence rate of foreign matters was 0.0 to 0.5%.

Comparison Example 1

The viscosity of the adhesive was adjusted to 10000 mPa·s with the content of the denatured aliphatic epoxy resin falling within a range of 15 to 25 wt %. The adhesive was cured by heating at 120 degrees C. for 20 mins.

As a result of having measured the sterilized adhesive, the occurrence rate of foreign matters was about 1 to 15%.

Comparison Table 1 in FIG. 4 indicates the measurement results of the respective Examples and the Comparison Example 1.

Apparently from these measurement results, it has been found that even higher viscosity of the adhesive did not obstruct the bonding workability between the injection needle and the needle-base member and that the occurrence rate of the foreign matters attributable to the adhesive could be greatly reduced to thereby largely enhance the yield by decreasing the content of the denatured aliphatic epoxy resin and increasing the viscosity of the adhesive.

(2) Relationship Between the Curing Temperature of the Adhesive and the Occurrence Rate of Foreign Matters Example 3

The viscosity of the adhesive was adjusted to 10000 mPa·s with the content of the denatured aliphatic epoxy resin falling within a range of 15 to 25 wt %. The adhesive was cured by heating at 130 degrees C. for 20 mins.

As a result of having measured the sterilized adhesive, the occurrence rate of foreign matters was 0.0 to 0.3%.

Example 4

The viscosity of the adhesive was adjusted to 20000 mPa·s with the content of the denatured aliphatic epoxy resin falling within a range of 15 to 25 wt %. The adhesive was cured by heating at 130 degrees C. for 20 mins.

As a result of having measured the sterilized adhesive, no foreign matter occurred.

Example 5

The viscosity of the adhesive was adjusted to 30000 mPa·s with the content of the denatured aliphatic epoxy resin falling within a range of 10 to 20 wt %. The adhesive was cured by heating at 130 degrees C. for 20 mins.

As a result of having measured the sterilized adhesive, no foreign matter occurred.

Comparison Table 2 in FIG. 5 indicates the measurement results of the respective Examples and the Comparison Example 1.

Apparently from the comparison of Example 3 with Comparison Example as to the measurement results, it has been found that even with the same content of the denatured aliphatic epoxy resin and the same viscosity of the adhesive, a higher curing temperature could largely alleviate the occurrence rate of the foreign matters attributable to the adhesive, thereby greatly enhancing the yield.

Further, apparently from the comparison of Examples 4 and 5 with Examples 1 and 2 as well as with Comparison Example 1, it has been found that it was possible to more alleviate the occurrence rate of the foreign matters to thereby more greatly enhance the yield by decreasing the content of denatured aliphatic epoxy resin and increasing the curing temperature.

The shape, dimension, structure, material of the syringe and of the front-assembly as well as the combined components, the combination ratio and the curing conditions of the adhesive, and the conditions of the sterilization treatment were only exemplified so as to realize the technical idea of the present invention and therefore various modifications can be added thereto within a scope of claims of the present invention. For instance, the needle-base member may be formed from stainless steel. As regards the curing temperature and heating time of the adhesive as well as the temperature and heating time of the sterilization treatment, they are not limited to those recited in Examples. Further, needless to say, the pharmaceutical medicine for injection to be filled into the injection cylinder is not limited to a specific pharmaceutical product.

INDUSTRIAL AVAILABILITY

The present invention can facilitates bonding the injection needle to the needle-base member and in addition can inhibit the occurrence of the foreign matters attributable to the adhesive to thereby enhance the yield. In consequence, it is suitably usable, for example, to the uni-chamber prefilled syringe and the dual-chamber prefilled syringe and also to the front-assembly used therefor. Needless to say, it is applicable to other syringes.

What is claimed is:

1. An adhesive composition for bonding a base end portion of an injection needle (4) to a needle-base member (5) at a leading end of an injection cylinder (2), said adhesive composition comprising: bisphenol A-type epoxy resin, denatured aliphatic epoxy resin, denatured polyamide resin, and titanium oxide; wherein:

the bisphenol A-type epoxy resin is provided in an amount of 35 to 50 wt % of the overall composition;

the denatured aliphatic epoxy resin is provided in an amount of 10 to 25 wt % of the overall composition;

the titanium oxide is provided in an amount of 10 to 20 wt % of the overall composition; and the composition has a viscosity of about 20000 mPa·s to about 40000 mPa·s during said bonding and prior curing.

2. The adhesive composition as set forth in claim 1, wherein the denatured aliphatic epoxy resin is provided in an amount of 15 to 25 wt % of the overall composition.

3. The adhesive composition as set forth in claim 1, wherein the denatured aliphatic epoxy resin is provided in an amount of 10 to 20 wt % of the overall composition.

4. A syringe front-assembly comprising an injection needle (4), a needle-base member (5), a connection hub (6) and a protector cap (7), the injection needle (4) being secured to the needle-base member (5), the needle-base member (5) being detachably attached to the connection hub (6), the connection hub (6) being provided with a connection portion (17) which is secured to the leading end of an injection cylinder (2), the protector cap (7) being removably fitted onto the injection needle (4) in such a manner that it covers a periphery of the injection needle (4), wherein the injection needle (4) and the needle-base member (5) are fixed to each other with the adhesive composition (19) as set forth in claim 1.

5. A syringe comprising an injection cylinder (2) which has a leading end additionally provided with a needle-base member (5), the injection needle (4) being fixed to the needle-base member (5), a protector cap being removably fitted onto the injection needle (4) in such a manner that it covers a periphery of the injection needle (4), wherein the injection needle (4) and the needle-base member (5) are fixed to each other with the adhesive composition (19) as set forth in claim 1.

* * * * *

UNITED STATES PATENT AND TRADEMARK OFFICE
CERTIFICATE OF CORRECTION

| | | |
|---|---|---|
| PATENT NO. | : 7,967,796 B2 | Page 1 of 1 |
| APPLICATION NO. | : 11/921574 | |
| DATED | : June 28, 2011 | |
| INVENTOR(S) | : Yuusuke Sakurai et al. | |

It is certified that error appears in the above-identified patent and that said Letters Patent is hereby corrected as shown below:

ON THE TITLE PAGE:

Item (73), Assignee: "Takeda Pharmaceutical Company" should read
--Takeda Pharmaceutical Company Limited--.

Signed and Sealed this
Thirtieth Day of August, 2011

David J. Kappos
*Director of the United States Patent and Trademark Office*